US009250304B2

(12) United States Patent  
Kang et al.

(10) Patent No.: US 9,250,304 B2  
(45) Date of Patent: Feb. 2, 2016

(54) MAGNETIC RESONANCE IMAGING (MRI) APPARATUS AND CONTROL METHOD THEREOF

(71) Applicant: Samsung Electronics Co., Ltd., Gyeonggi-do (KR)

(72) Inventors: Jeong A Kang, Gyeonggi-do (KR); Keum Yong Oh, Gyeonggi-do (KR); I Hwa Choi, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 172 days.

(21) Appl. No.: 13/954,420

(22) Filed: Jul. 30, 2013

(65) Prior Publication Data

US 2014/0086421 A1    Mar. 27, 2014

(30) Foreign Application Priority Data

Sep. 25, 2012    (KR) .................. 10-2012-0106814

(51) Int. Cl.
| | |
|---|---|
| H03G 3/20 | (2006.01) |
| G01R 33/28 | (2006.01) |
| A61B 5/00 | (2006.01) |
| A61B 5/055 | (2006.01) |
| H03G 3/00 | (2006.01) |
| H03F 99/00 | (2009.01) |

(52) U.S. Cl.
CPC .............. *G01R 33/283* (2013.01); *A61B 5/055* (2013.01); *A61B 5/7405* (2013.01); *G01R 33/288* (2013.01)

(58) Field of Classification Search
CPC .......... G10R 33/283; H03G 3/32; H03G 7/00; H04R 5/04
USPC ............. 381/57, 28, 101, 102, 104, 106, 107, 381/120
See application file for complete search history.

(56) References Cited

U.S. PATENT DOCUMENTS

| 4,696,030 | A | * | 9/1987 | Egozi ................... 379/167.01 |
| 5,384,537 | A | * | 1/1995 | Ito et al. .................. 324/318 |
| 5,552,708 | A | * | 9/1996 | Ham ....................... 324/318 |
| 2008/0118077 | A1 | | 5/2008 | Rasmussen |

FOREIGN PATENT DOCUMENTS

| EP | 0 655 730 A1 | 5/1995 |
| JP | 2011-194178 A | 10/2011 |

* cited by examiner

*Primary Examiner* — Paul S Kim  
*Assistant Examiner* — Norman Yu  
(74) *Attorney, Agent, or Firm* — Cha & Reiter, LLC (57) ABSTRACT

A magnetic resonance imaging (MRI) apparatus and control method for comparing a sound generated from the bore of the MRI apparatus to a pulse sequence sound to adjust the output level of a sound output unit located in an operating room and thus permit a patient to be heard by an operator when an emergency situation or other information is expressed by the patient. The magnetic resonance imaging (MRI) apparatus includes: a sound input unit; a sound output unit configured to output a sound acquired by the sound input unit; and a controller configured to compare the acquired sound to a sound of a pulse sequence stored in advance, and to increase the output level of the sound output unit if the acquired sound is not identical to the sound of the pulse sequence.

17 Claims, 11 Drawing Sheets

MAGNETIC RESONANCE IMAGING (MRI) APPARATUS AND CONTROL METHOD THEREOF

CLAIM OF PRIORITY

This application claims the benefit of priority under 35 U.S.C. §119 from Korean Patent Application No. 10-2012-0106814, filed on Sep. 25, 2012 in the Korean Intellectual Property Office, the disclosure of which is incorporated herein by reference.

BACKGROUND

1. Field of the Invention

The present disclosure relates to a magnetic resonance imaging (MRI) apparatus for diagnosing various diseases using MRI, and a control method thereof. More particularly, the present disclosure relates to sounds emitted by the MRI during operation.

2. Description of the Related Art

In general, a medical imaging system is an apparatus for providing information about an internal area of a patient as an image. In general, medical imaging systems include, for example, an X-ray machine, an ultrasonic diagnostic instrument, a computer tomography (CT) scanner, a magnetic resonance imaging (MRI) apparatus, etc.

The MRI apparatus holds an important position in the field of medical imaging diagnosis because image-taking conditions are relatively free and can provide excellent detectability and various diagnosis information images with respect to soft tissue.

The MRI causes nuclear magnetic resonance (NMR) in the hydrogen atomic nuclei of the human body using a magnetic field harmless to humans and RF which is non-ionizing radiation, to thus image the densities and physical or chemical characteristics of the atomic nuclei.

In more detail, the MRI apparatus supplies a specific frequency and energy to atomic nuclei in the state in which a constant magnetic field has been applied to the atomic nuclei, to cause the atomic nuclei to release energy, and converts the energy released from the atomic nuclei to signals, thereby diagnosing the inside human body.

When a magnetic field is applied, protons configuring atomic nuclei are arranged in the direction of the magnetic field since they have spin angular momentum and magnetic dipole moment, and the atomic nuclei perform precession with respect to the direction of the magnetic field. The precession causes nuclear magnetic resonance so that an image of the inside human body can be acquired through the nuclear magnetic resonance.

Meanwhile, scanning using a MRI apparatus generally generates a loud noise of about 100 dB. The loud noise that is generated upon scanning using the MRI apparatus is mainly due to the vibration of coils by the Lorentz force that is generated when current is applied to gradient coils in order to form gradient magnetic fields suitable for a specific scanning protocol.

Due to the noise generated by the MRI apparatus, during the scanning period from about 30 minutes to about 1 hour, an operator in an operating room turns down the volume of a speaker connected to a microphone located in a scan room to zero when he or she determines that conversation with a patient is unnecessary so as not to listen to noise captured by the microphone.

However, in the case where the operator turns the speak volume to zero, a problem arises when the patient wants to communicate with the operator because he or she feels discomfort or an emergency situation has occurred, the patient cannot communicate with the operator.

SUMMARY

Therefore, it is an aspect of the present invention to provide a magnetic resonance imaging (MRI) apparatus for comparing a sound generated in the bore of the MRI apparatus to a pulse sequence sound in order to adjust the output level of a sound output unit located in an operating room, and a control method of the MRI apparatus according to the present invention.

Additional aspects of the invention will be set forth in part in the description which follows and, in part, will assist a person of ordinary skill in the art to better understand the invention from the description, or may be learned by practice of the invention.

In accordance with one exemplary aspect of the present invention, a magnetic resonance imaging (MRI) apparatus can include: a sound input unit located in a bore; a sound output unit located in a workstation and configured to output a sound acquired by the sound input unit; and a controller configured to compare the acquired sound to a pulse sequence sound stored in advance, and to increase the output level of the sound output unit when the acquired sound is not identical to the pulse sequence sound.

According to an exemplary aspect of the invention, if the acquired sound is identical to the sound of the pulse sequence, the controller can decrease the output level of the sound output unit to a predetermined level.

The MRI apparatus can further include a sequence sound database configured to store patterns of sounds that are respectively generated for a plurality of pulse sequences registered in the MRI apparatus when a subject is scanned according to at least one of the pulse sequences.

The controller can check a pulse sequence being used to scan a subject, receive a sound generated in a bore from the sound input unit, compare the received sound to a sound of the checked pulse sequence, and increase the output level of the sound output unit to a predetermined level when the pattern of the received sound is not identical to the pattern of the checked pulse sequence sound.

If the pattern of the acquired sound is not identical to the pattern of the pulse sequence sound, the controller can eliminate a part corresponding to the pulse sequence sound from the acquired sound, increase the output level of the sound output unit to a predetermined level, and output the sound from which the pulse sequence sound has been eliminated, through the sound output unit whose output level has increased to the predetermined level.

In addition, if the pattern of the acquired sound is not identical to the pattern of the pulse sequence sound, the controller can eliminate a part corresponding to the pulse sequence sound from the acquired sound, determine whether the sound from which the pulse sequence sound has been eliminated is identical to a subject's voice stored in advance, increase the output level of the sound output unit to a predetermined level when the sound from which the pulse sequence sound has been eliminated is identical to the subject's voice, and output the sound from which the pulse sequence sound has been eliminated, through the sound output unit whose output level has increased to the predetermined level.

On the other hand, if the controller determines that the pattern of the acquired sound is identical to the pattern of the pulse sequence sound after increasing the output level of the sound output unit, the controller can then decrease the output level of the sound output unit to an original level to which the sound output unit has been set before the output level of the sound output unit increases.

The sound input unit may include a microphone, and may be located in the inside space of the bore in which a subject is located.

Also, a sound output unit for outputting a sound transferred from the workstation may be provided in the inside space of the bore, and the sound output unit can include a speaker.

Additionally, the sound output unit can include, for example, a speaker, a sound input unit for allowing an operator to input a sound to be transferred to the bore may be provided in the workstation, and the sound input unit can include a microphone.

In accordance with another exemplary aspect of the present invention, a sound output apparatus can include: a receiving unit configured to receive a sound; an output unit configured to output the sound received by the receiving unit; and an output adjusting unit configured to compare the received sound to a sound of a pulse sequence stored in advance, and to increase the output level of the output unit when the received sound is not identical to the sound of the pulse sequence.

In accordance with another exemplary aspect of the present invention, a control method of a magnetic resonance imaging (MRI) apparatus can include: comparing by a controller a sound acquired by a sound input unit located in a bore to a pulse sequence sound stored in advance; and increasing the output level of a sound output unit located in a workstation to a predetermined level if the acquired sound is not identical to the pulse sequence sound.

The control method can further include decreasing the output level of the sound output unit to a predetermined level if the acquired sound is identical to the sound of the pulse sequence.

The comparing of the acquired sound to the sound of the pulse sequence stored in advance can include: receiving a sound generated in a bore from the sound input unit; determining a pulse sequence sound that is to be compared to the received sound; and comparing the received sound to the decided pulse sequence sound.

The determining of the pulse sequence sound that is to be compared to the received sound can include: checking a pulse sequence being used to scan a subject; and determining a sound of the checked pulse sequence with reference to sequence sound database in which patterns of sounds that are respectively generated for a plurality of pulse sequences are stored.

The increasing of the output level of the sound output unit to the predetermined level can include: determining whether the acquired sound is identical to the sound of the pulse sequence; eliminating a part of the sound corresponding to the sound of the pulse sequence from the acquired sound when the pattern of the acquired sound is not identical to the pattern of the pulse sequence sound; and increasing the output level of the sound output unit to a predetermined level in order to output the sound from which the sound of the pulse sequence has been eliminated.

The increasing of the output level of the sound output unit to the predetermined level can include: determining whether the acquired sound is identical to the sound of the pulse sequence; eliminating a part of the sound corresponding to the pulse sequence sound from the acquired sound if the pattern of the acquired sound is not identical to the pattern of the pulse sequence sound; determining whether the sound from which the pulse sequence sound has been eliminated is identical to a subject's voice stored in advance; and increasing the output level of the sound output unit to a predetermined level when the sound from which the pulse sequence sound has been eliminated is identical to the subject's voice, in order to output the sound from which the pulse sequence sound has been eliminated.

The control method can further include determining whether the acquired sound is identical to the pulse sequence sound after increasing the output level of the sound output unit to the predetermined level, and decreasing, if the acquired sound is identical to the pulse sequence sound, the output level of the sound output unit to an original level to which the sound output unit has been set before the output level of the sound output unit increases.

The sound input unit can include, for example a microphone, and may be located in the inside space of the bore in which a subject is located.

In addition, a sound output unit for outputting a sound transferred from the workstation may be provided in the inside pace of the bore, and the sound output unit can include a speaker. The sound input unit for allowing an operator to input a sound to be transferred to the bore may be provided in the workstation, and the sound input unit may include a microphone.

According to an exemplary aspect of the present invention, while a patient is scanned using the MRI apparatus, bidirectional communication can be performed between the patient and an operator.

Also, workflow is improved because the volume of a speaker is automatically adjusted without having to manually adjusting a sound output unit, so that an operator can concentrate his or her attention on scanning.

BRIEF DESCRIPTION OF THE DRAWINGS

These and/or other exemplary aspects of the invention will become apparent and more readily appreciated from the following description of the embodiments, taken in conjunction with the accompanying drawings of which.

DETAILED DESCRIPTION

Reference will now be made in detail to some exemplary embodiments of the present invention, examples of which are illustrated in the accompanying drawings, wherein like reference numerals refer to like elements throughout. An artisan should understand and appreciate that the claimed invention is not limited to any examples shown and described herein.

Figure 1:
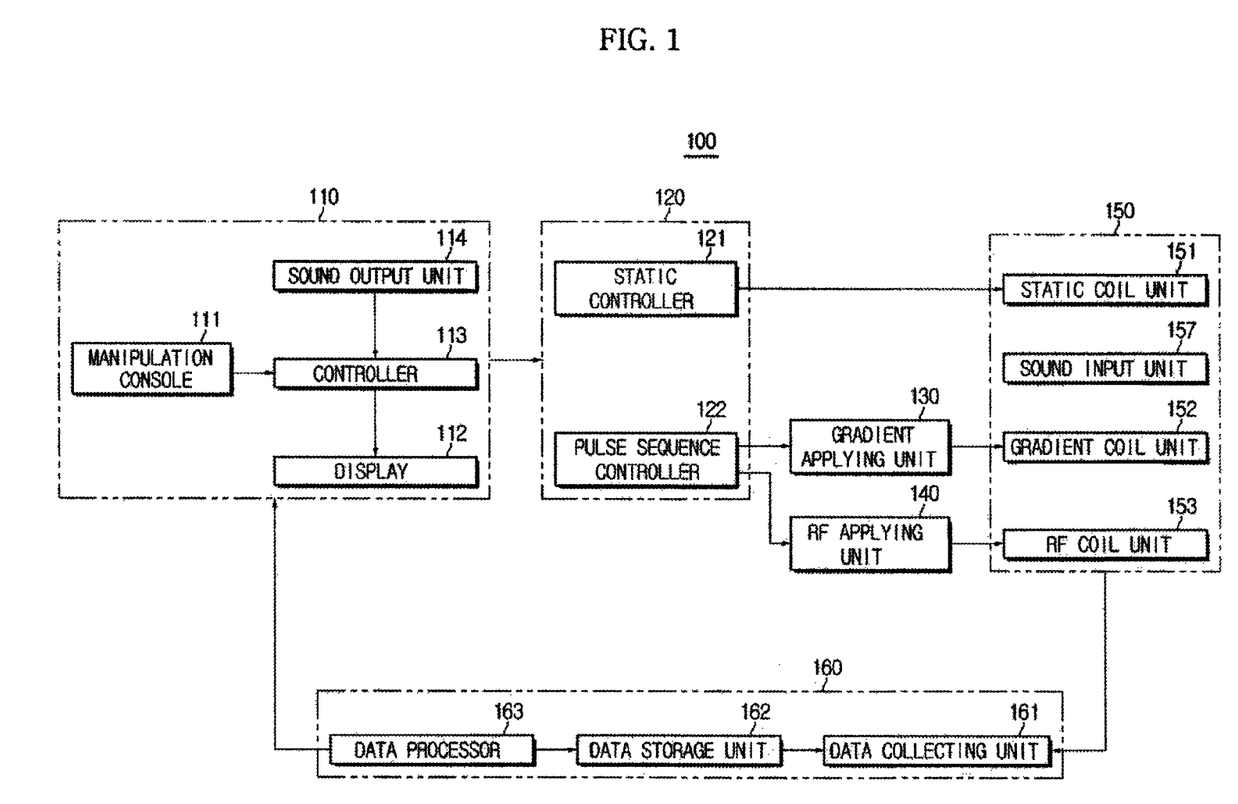
FIG. 1 is a control block diagram of a magnetic resonance imaging (MRI) apparatus in accordance with an exemplary embodiment of the present invention.

FIG. 1 is a control block diagram of a magnetic resonance imaging (MRI) apparatus 100 in accordance with one embodiment of the present invention.

Referring now to FIG. 1, the MRI apparatus 100 in accordance with an exemplary embodiment of the present invention can include a bore 150 for forming a magnetic field and generating resonance with respect to atomic nuclei, a coil controller 120 for controlling the operation of coils configuring the bore 150, an image processor 160 for receiving echo signals generated from the atomic nuclei to create a magnetic resonance image, and a workstation 110 for controlling the entire operation of the MRI apparatus 100.

The bore 150 includes, for example, a static coil unit 151 for forming a static field there inside, a gradient coil unit 152 for forming gradient fields in the static field, a RF coil unit 153 for applying RF pulses to excite atomic nuclei and receiving echo signals from the atomic nuclei, and a sound input unit 157 provided inside the bore 150 to acquire a sound generated in the bore 150 in which a subject is also located.

The coil controller 120 preferably includes a static controller 121 for controlling the strength and direction of a static field that is formed by the static coil unit 151, and a pulse sequence controller 122 for designing a pulse sequence and controlling the gradient coil unit 152 and the RF coil unit 153 according to the pulse sequence. The coil controller includes circuitry such as a processor, microprocessor, etc.

Also, the MRI apparatus 100 includes a gradient applying unit 130 that outputs a gradient signal to the gradient coil unit 152, and a RF applying unit 140 for applying an RF signal to the RF coil unit 153, so that the pulse sequence controller 122 controls the gradient applying unit 130 and the RF applying unit 140 to adjust a gradient field that is formed in a static field and RF that is applied to atomic nuclei.

In addition, the MRI apparatus 100 can include the workstation 110 through which an operator can manipulate the MRI apparatus 100 and which receives control commands regarding the operation of the MRI apparatus 100 from the operator.

The workstation 110 can include a manipulation console 111 for allowing the operator to manipulate the MRI apparatus 100, a display 112 for displaying a control state and displaying an image created by the image processor 160 in order for the user to diagnose the health state of a subject 200, a sound output unit 114 for outputting a sound acquired by the sound input unit 157 located in the bore 150, and a controller 113 configured for comparing the sound acquired by the sound input unit 157 to a pulse sequence sound and adjust the output level of the sound output unit 114 according to the result of the comparison. Operation in which the controller 113 adjusts the output level of the sound output unit 114 will be described in detail later.

Figure 2:
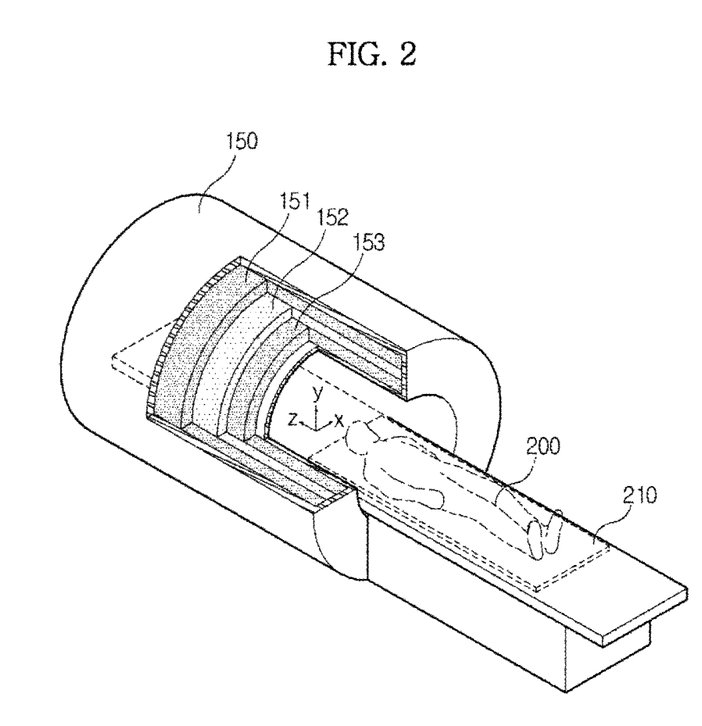
FIG. 2 schematically shows the appearance of the MRI apparatus.
Figure 3:
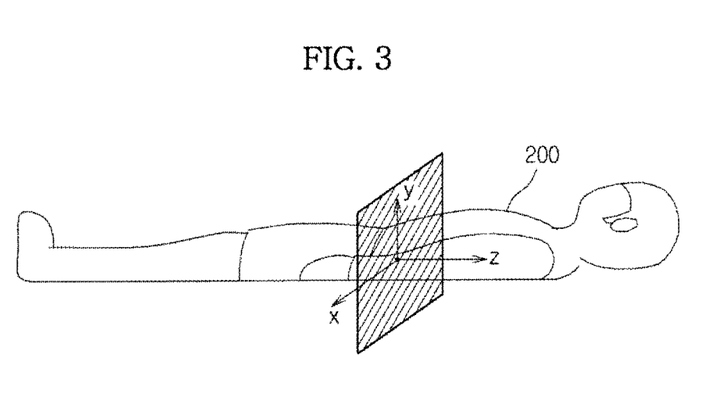
FIG. 3 shows a subject lying in a space divided to x, y, and z axes.
Figure 4:
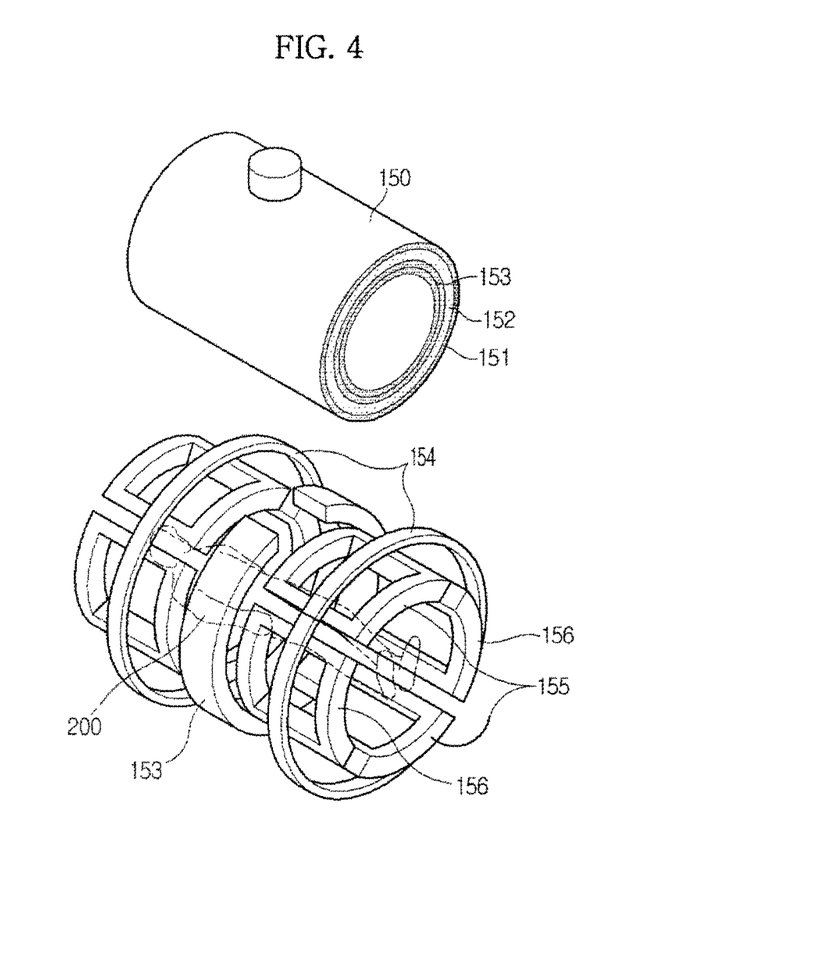
FIG. 4 shows the structures of a bore and a gradient coil unit of the MRI apparatus.
Figure 5:
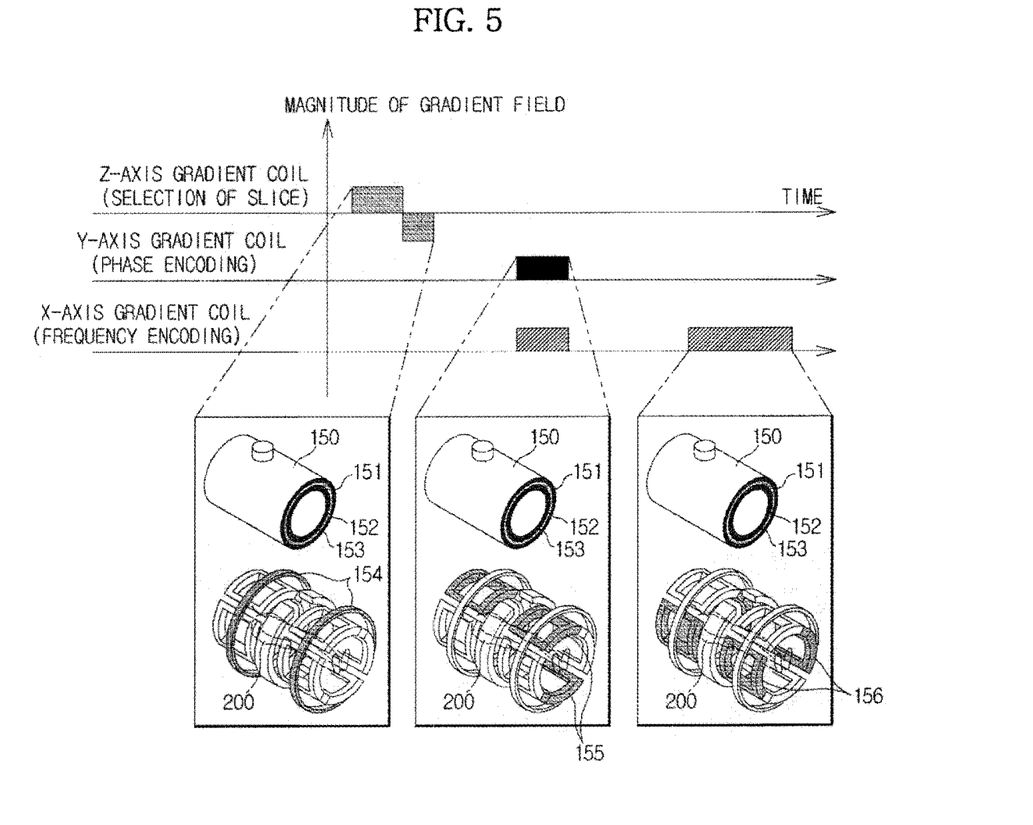
FIG. 5 shows individual gradient coils configuring the gradient coil unit and pulse sequences related to operation of the individual gradient coils.

FIG. 2 schematically shows a perspective view of the MRI apparatus 100 having some of the external structure cut away, FIG. 3 shows a subject lying in a space divided to x, y, and z axes, and FIG. 4 shows exemplary structures of the bore 150 and the gradient coil unit 152, and FIG. 5 shows exemplary structures of individual gradient coils configuring the gradient coil unit 152 and pulse sequences related to operation of the individual gradient coils.

Hereinafter, the operation of the MRI apparatus 100 will now be described in detail with reference to FIG. 1.

The bore 150 is in the shape of a hollow cylinder, and the inside space of the bore 150 is referred to as cavity. A transfer unit 210 moves the subject 200 lying thereon to the cavity in order to obtain a magnetic resonance signal.

The bore 150 in this example includes a static coil unit 151, a gradient coil unit 152, and an RF coil unit 153.

The static coil unit 151 can have a structure in which coils are wound around the cavity, and when current is applied to the static coil unit 151, a static field is formed inside the bore 150, that is, in the cavity.

The direction of the static field is generally parallel to the concentric axis of the bore 150.

If the static field is formed in the cavity, the atomic nuclei of atoms (specifically, hydrogen atoms) configuring the subject 200 are arranged in the direction of the static field, and perform precession with respect to the direction of the static field. The precession speed of the atomic nuclei can be expressed, for example, as a precession frequency, which is called a Larmor frequency, and may be represented by equation 1, below.

$$\omega = \gamma B_0, \quad (1)$$

where $\omega$ is the Larmor frequency, $\gamma$ is a proportional constant, and $B_0$ is the strength of an external magnetic field. The proportional constant depends on the kind of atomic nuclei, the strength of the external magnetic field is measured in units of Tesla (T) or Gauss (G), and the precession frequency is measured in units of Hz.

For example, hydrogen protons have a precession frequency of 42.58 MHz in an external magnetic field of 1 T. Since hydrogen atoms constitute a main portion of atoms configuring the human body, the MRI acquires a magnetic resonance signal using the precession of hydrogen protons.

The gradient coil unit 152 generates a gradient in the static field formed in the cavity to form a gradient magnetic field.

As shown in FIG. 3, an axis parallel to the up and down direction from head to feet of the subject 200, that is, an axis parallel to the direction of the static field may be determined to be the z-axis, an axis parallel to the left and right direction of the subject 200 may be determined to be the x-axis, and an axis parallel to the up and down direction in the 3-dimensional (3D) space may be determined to be the y-axis.

In order to obtain 3D spatial information, gradient magnetic fields with respect to all of the x-, y-, and z-axes are required. Accordingly, the gradient coil unit 152 includes three pairs of gradient coils.

As shown in FIGS. 4 and 5, z-axis gradient coils 154 are configured with a pair of ring-shaped coils, and y-axis gradient coils 155 are positioned above and below the subject 200. Also, x-axis gradient coils 156 are positioned in the left and right sides of the subject 200.

If direct currents having opposite polarities flow through the respective z-axis gradient coils 154, a change of a magnetic field in the z-axis direction occurs so that a gradient magnetic field is formed. FIG. 5 shows a pulse sequence corresponding to a z-axis gradient magnetic field formed when the z-axis gradient coils 154 are in operation.

Since the greater gradient of the gradient magnetic field formed in the z-axis direction enables the thinner slice to be selected, the z-axis gradient coils 154 are used to select a slice.

If a slice is selected through the gradient magnetic field formed by the z-axis gradient coils 154, spins configuring the corresponding slice have the same frequency and phase, so that the individual spins cannot be distinguished from each other.

In this state where spins configuring the corresponding slice have the same frequency and phase, if a gradient magnetic field in the y-axis direction is formed by the y-axis gradient coils 155, the y-axis gradient magnetic field causes a phase shift such that the rows of the slice have different phases.

More particularly, if the y-axis gradient magnetic field is formed, the phases of the spins of rows to which the greater gradient magnetic field has been applied change to the higher frequencies, and the phases of the spins of rows to which the smaller gradient magnetic field has been applied change to the lower frequencies. Thereafter, if the y-axis gradient magnetic field disappears, phase shift occurs in the individual rows of the selected slice so as for the rows to have different phases, in order for the rows to be distinguished from each other. As such, the gradient magnetic field formed by the y-axis gradient coils 155 is used for phase encoding. FIG. 5 also shows a pulse sequence corresponding to the y-axis gradient magnetic field formed when the y-axis gradient coils 155 operate.

In summary, a slice is selected through the gradient magnetic field formed by the z-axis gradient coils 154, and rows configuring the selected slice are distinguished to have different phases through the gradient magnetic field formed by the y-axis gradient coils 155. However, spins configuring each row still cannot be distinguished since they have the same frequency and phase.

In this state, if a gradient magnetic field in the x-axis direction is formed by the x-axis gradient coils 156, the x-axis gradient magnetic field causes spins configuring each row to have different frequencies such that the spins configuring each row can be distinguished from each other. As such, the gradient magnetic field formed by the x-axis gradient coils 156 is used for frequency encoding.

As described above, the gradient magnetic fields respectively formed by the z-, y-, and x-axis gradient coils spatially encode the spatial locations of individual spins through slice selection, phase encoding, and frequency encoding.

With reference again to FIG. 1, the gradient coil unit 152 is connected to the gradient applying unit 130, and the gradient applying unit 130 applies (outputs) a driving signal to the gradient coil unit 152 according to a control signal received from the pulse sequence controller 122 to generate gradient magnetic fields. The gradient applying unit 130 can include three driving circuits in correspondence to three types of gradient coils 154, 155, and 156 configuring the gradient coil unit 152.

As described above, atomic nuclei arranged by an external magnetic field perform precession at the Larmor frequency, and a sum of magnetization vectors of some atomic nuclei may be represented as net magnetization "M".

The z-axis component of the net magnetization M cannot be measured, and only $M_{xy}$ can be detected. Accordingly, in order to obtain a magnetic resonance signal, the atomic nuclei should be excited so that net magnetization M exists on the xy plane. For excitation of atomic nuclei, it is necessary to apply a RF pulse tuned to the Larmor frequency of the atomic nuclei to the static field.

The RF coil unit 153 includes a transmission coil for transmitting the RF pulse, and a reception coil for receiving electromagnetic waves, that is, a magnetic resonance signal released from excited atomic nuclei The RF coil unit 153 is connected to the RF applying unit 140, and the RF applying unit 140 applies (outputs) a driving signal to the RF coil unit 153 according to a control signal received from the pulse sequence controller 122 so that the RF coil unit 153 transmits the RF pulse.

The RF applying unit 140 includes circuitry such as a modulation circuit for modulating a high frequency output signal to a pulse type signal, and a RF power amplifier for amplifying the pulse type signal.

Also, the RF coil unit 153 is connected to the image processor 160, and the image processor 160 can include a data collecting unit 161 for receiving data regarding a magnetic resonance signal generated from atomic nuclei, and a data processor 163 for processing data collected by the data collecting unit 161 to create a magnetic resonance image.

The data collecting unit 161 includes circuitry such as a preamplifier for amplifying the magnetic resonance signal received by the reception coil of the RF coil unit 153, a phase detector for receiving the magnetic resonance signal from the preamplifier to detect the phase of the magnetic resonance signal, and an A/D converter for converting the analog signal acquired by the phase detection to a digital signal. Also, the data collecting unit 161 transmits the digitalized magnetic resonance signal to a data storage unit 162.

In the data storage unit 162, a data space configuring a 2D Fourier space is formed, and after scanned data is all stored in the data storage unit 162, the data processor 163 performs 2D Inverse-Fourier Transform on data in the 2D Fourier space to reconfigure an image about the subject 200. The reconfigured image is displayed on the display 112.

In a method for acquiring a magnetic resonance signal from atomic nuclei, a spin echo pulse sequence has been widely used. If the RF coil unit 153 sequentially applies two RF pulses with a predetermined time interval Δt in between, strong transverse magnetization occurs in atomic nuclei when the time interval Δt has again elapsed, and a magnetic resonance signal may be acquired through the strong transverse magnetization. This method is called a spin echo pulse sequence. A time period taken until the magnetic resonance signal is generated from when the first RF pulse has been applied is time echo (TE).

A degree at which protons have been flipped can be represented as an angle at which the protons have moved away from an axis on which they have been positioned before flipped, and the corresponding RF pulse may be represented as a, for example, 90° RF pulse, a 180° RF pulse, etc., according to the degree of flip.

Figure 6:
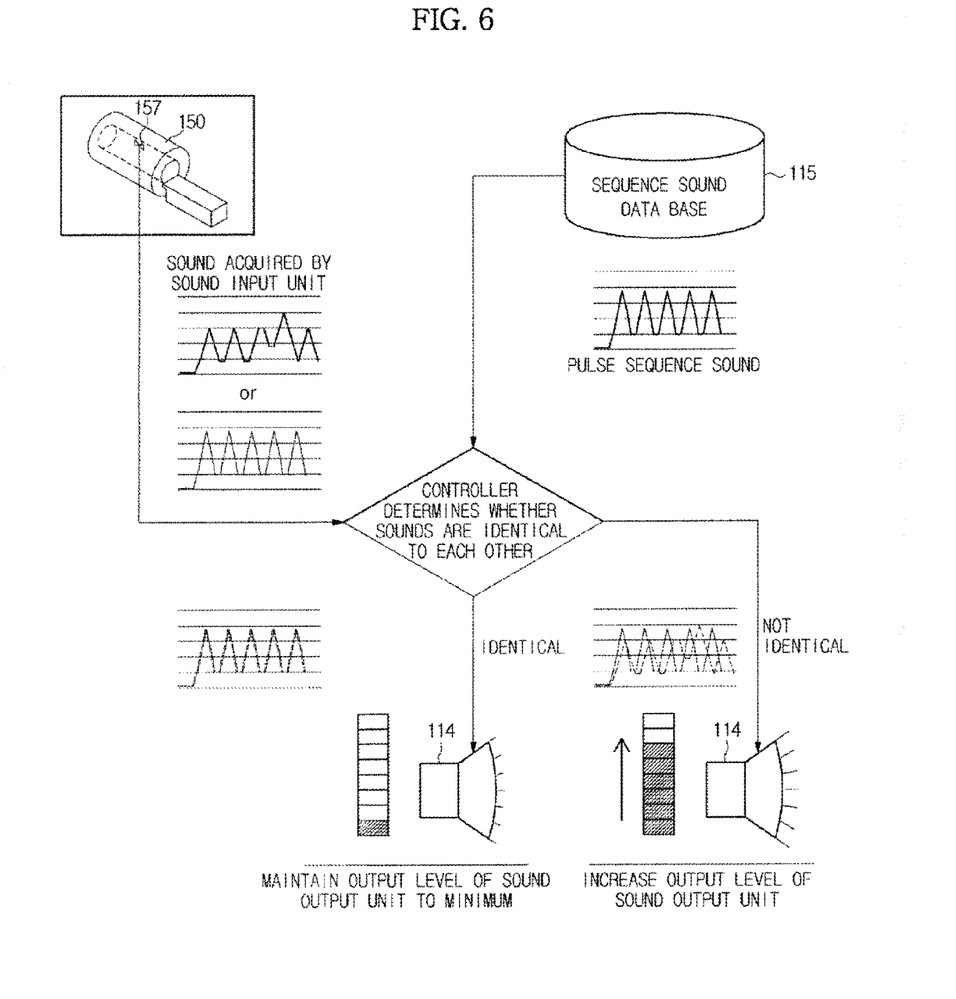
FIG. 6 is a view illustrating an exemplary process of controlling the output level of a sound output unit in the MRI apparatus.
Figure 7:
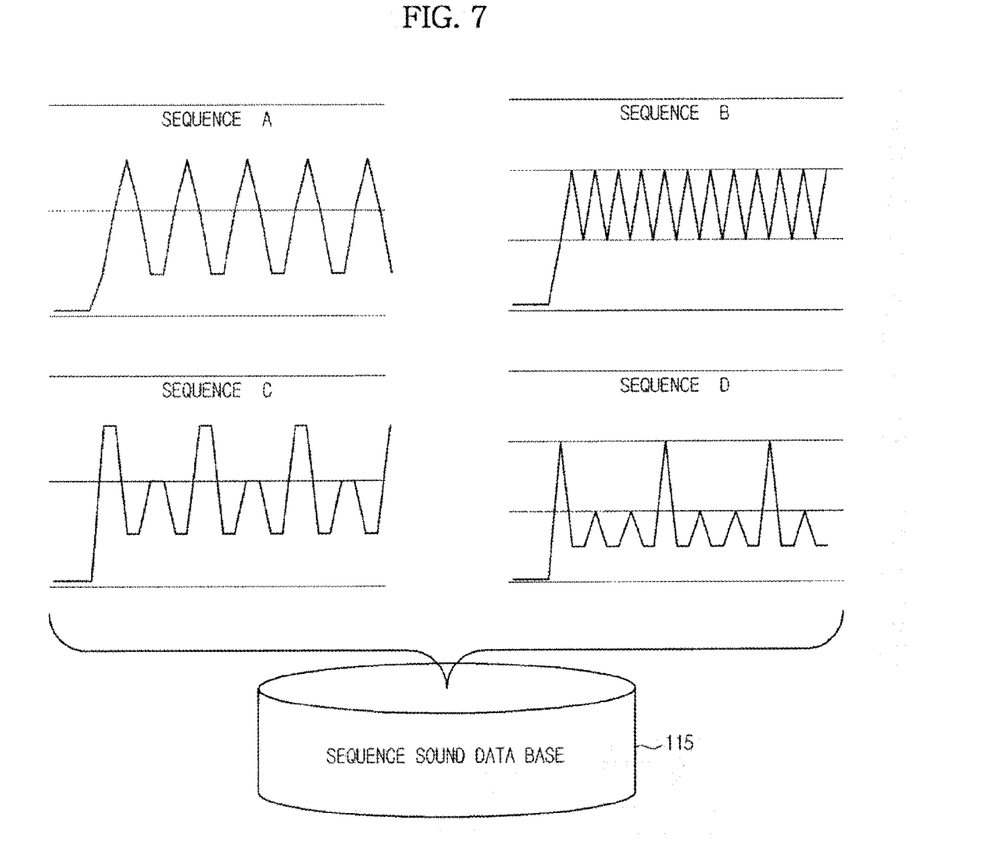
FIG. 7 shows sound signals for individual pulse sequences that are stored in advance in sequence sound database.
Figure 8:
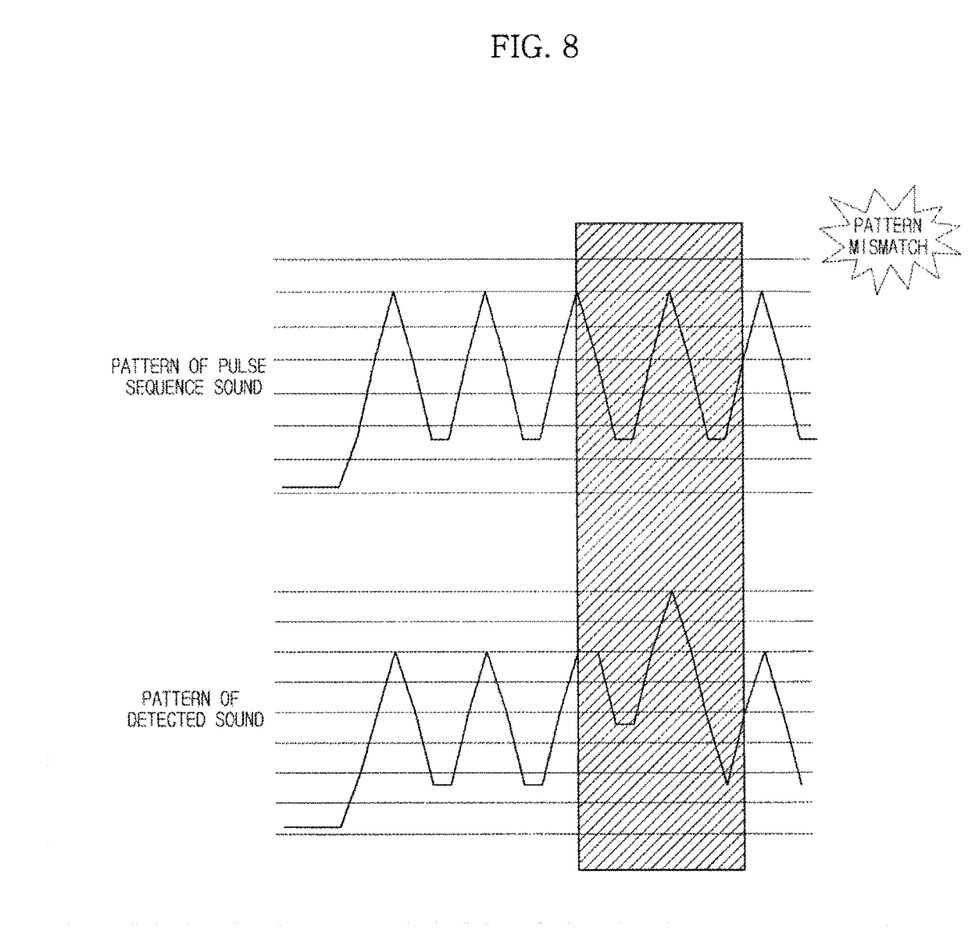
FIG. 8 shows an area at which the pattern of a sound acquired by a sound input unit is not identical to the pattern of a pulse sequence sound.
Figure 9:
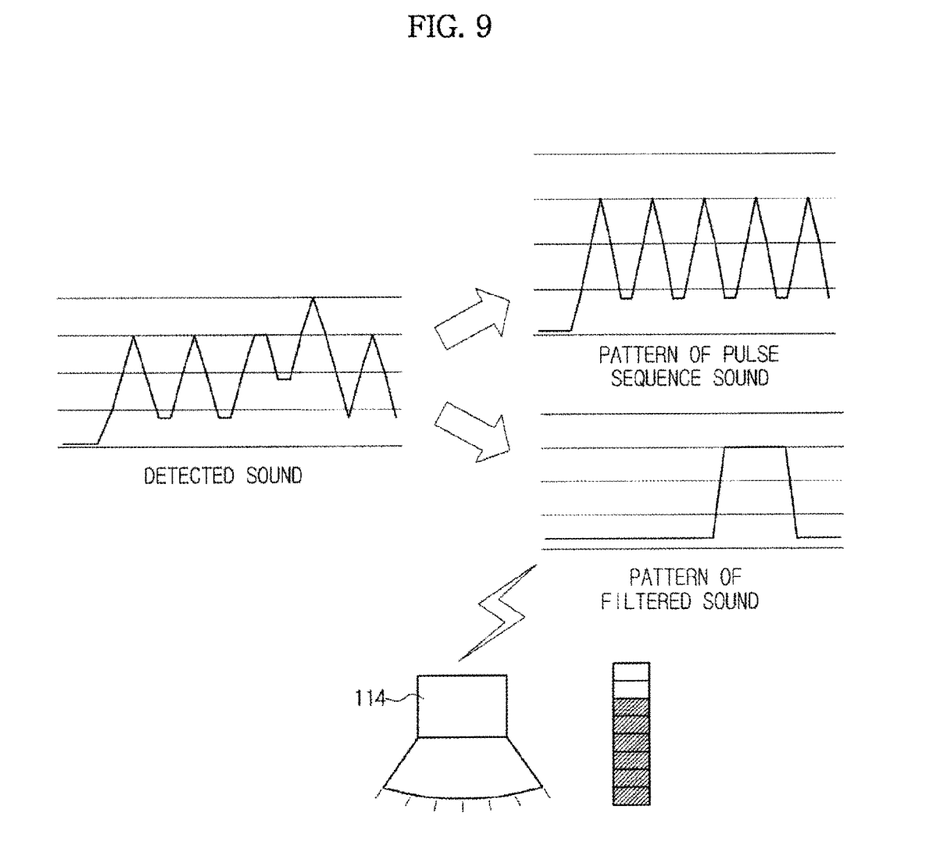
FIG. 9 is a view illustrating operation of outputting a sound filtered by eliminating a part corresponding to a pulse sequence sound from a sound acquired by the sound input unit, through a sound output unit whose volume level has been turned up.

FIG. 6 is a illustrates a process of controlling the output level of the sound output unit 114 in the MRI apparatus 100, FIG. 7 shows sound signals for individual pulse sequences that are stored in advance in the sequence sound database 115, FIG. 8 shows an area at which the pattern of a sound acquired by the sound input unit 157 is not identical (mismatch) to the pattern of a pulse sequence sound, and FIG. 9 is illustrates operation of outputting a sound filtered by eliminating a part corresponding to a pulse sequence sound from a sound acquired by the sound input unit 157, through a sound output unit whose volume level has been turned up.

The sound input unit 157, which is typically located in the cavity of the bore 150, acquires sounds generated when the MRI apparatus 100 is driven, and the acquired sounds are converted to electrical signals and transferred to the workstation 110 (see FIG. 1) located in a scan room. The signals are output as sounds through the sound output unit 114 located in the workstation 110.

Generally, sounds that are generated when a MRI apparatus is driven is due to the vibration of coils by the Lorentz force that is generated when a current is applied to gradient coils in order to form gradient magnetic fields suitable for a specific scanning protocol.

In other words, the sounds acquired by the sound input unit 157 are mainly due to driving of the gradient coil unit. Sounds that are generated by pulse sequences corresponding to driving patterns of the gradient coil unit have predetermined patterns.

Accordingly, sounds corresponding to the predetermined patterns of pulse sequences are catalogued in a database to establish the sequence sound database 115, and the database 115 is stored in advance in the workstation 110 in order for the controller 113 (see FIG. 1) to adjust the output level of the sound output unit 114 with reference to the database 115.

As described above, since a sound acquired by the sound input unit 157 is a sound generated by the gradient coil unit that is driven according to a pulse sequence, the sound will have the same pattern as a sound of the corresponding pulse sequence stored in the sequence sound database 115.

However, if a different sound from sounds that are generated by driving of the gradient coil unit is generated, the pattern of a sound acquired by the sound input unit 157 will be different from the pattern of a sound that is generated by the corresponding pulse sequence.

For example, if the sound input unit 157 has acquired a sound generated when a patient has spoken or taken a certain action or actions in order to inform the operator of discomfort or an emergency situation during scanning, the pattern of the acquired sound becomes different from the pattern of a sound that is generated by the corresponding pulse sequence.

Generally, since noise that is generated by a pulse sequence is very loud and not comparable to a voice, operators tend to do a scan after setting the volume of the sound output unit 114 (that is, a speaker) located in the workstation 110 to nearly zero. However, in this case, when the patient speaks in order to inform the operator of an emergency situation (or speaks for some other reason), an operator cannot respond to the patient. Accordingly, the MRI apparatus 100 according to the present exemplary embodiment provides a method of comparing a sound acquired by the sound input unit 157 to a pulse sequence sound to automatically adjust the output level of the sound output unit 114 according to the result of the comparison.

Referring now to FIG. 6, the sound input unit 157 located in the cavity of the bore 150, a microphone acquires a sound generated in the bore 150 when a subject is scanned, and transfers the acquired sound to the controller 113 of the workstation 110.

As described above, the sound acquired by the sound input unit 157 may be a sound generated by a pulse sequence being used to scan the subject, or a mixed sound in which another sound, such as a patient's voice, etc., that is mixed with the sound generated by the corresponding pulse sequence.

If the controller 113 of the workstation 110 receives the sound generated in the bore 150 from the sound input unit 157, the controller 113 searches for a sound in the sequence sound database 115 that is to be compared to the received sound. More particularly, the controller 113 searches in the sequence sound database 115 for sound information about a pulse sequence being currently used to scan the subject, and determines the found sound as a sound that is to be compared to the sound received from the sound input unit 157.

As shown in FIG. 7, the sequence sound database 115 stores sounds that are generated by various kinds of pulse sequences (e.g. sequence A, B, C, D, etc.) registered in the MRI apparatus (100 of FIG. 1) to be used to scan a subject.

Since sounds that are generated by the same pulse sequence make the same pattern of sound, the database 115 can be established by storing sounds of individual pulse sequences.

After a pulse sequence sound is determined, the controller 113 compares the sound received from the sound input unit 157 to the pulse sequence sound to determine whether the received sound is identical to the pulse sequence sound.

FIG. 8 shows an area at which the pattern of the sound received from the sound input unit 157 is not identical to the pattern of the pulse sequence sound.

If another sound, such as a patient's voice, etc., is mixed with the pulse sequence sound, the sound acquired by the sound input unit 157 has a different pattern from that of the pulse sequence sound.

If the controller 113 determines that the pattern of the received sound is not identical to the pattern of the pulse sequence sound (i.e. a "pattern mismatch"), the controller 113 increases the output level of the sound output unit 114 located in the workstation 110 to a predetermined level in order to inform the operator of the generation of a different sound from the pulse sequence sound in the bore 150.

Generally, the output level of the sound output unit 114 is set to a minimum level close to zero. Since noise that is generated by a pulse sequence is very loud, an operator will not be able to concentrate his or her attention on scanning a subject while the noise is being directly output to an operating room through the sound output unit 114, increasing a potential for the operator to fail to properly scan the subject.

However, since a pattern mismatch between the two sounds means that a sound other than the pulse sequence sound has been generated (pulse sequence generated sound) in the bore 150, which increases the probability that the patient experiences an unexpected situation, so it is therefore necessary to transfer the sound acquired by the sound input unit 157 through the sound output unit 114 so that the operator can recognize the situation. Accordingly, the output level of the sound output unit 114 which has outputted sounds at a low output level increases to the predetermined level. The predetermined level may be set to an appropriate level at which the operator can recognize a sound.

Meanwhile, if the patterns of the two sounds are identical to each other when the output level of the sound output unit 114 has been set to a normal output level, instead of the minimum level close to zero, this means that only the sound caused by the pulse sequence has been generated, and accordingly, the output level of the sound output unit 114 decreases to the minimum level close to zero.

FIG. 9 is a illustrates an exemplary operation of eliminating a part corresponding to a pulse sequence sound from a sound acquired by the sound input unit 157 to filter sounds generated by different causes, not by the pulse sequence.

Since a sound that will be transferred to the operator through the sound output unit 114 needs not to include the pulse sequence sound, the pulse sequence sound is eliminated from the sound acquired by the sound input unit 157 such that only sounds generated by other causes, not by the pulse sequence are output through the sound output unit 114. This filtering makes the sounds generated by other causes to be more audible by the operator.

In other words, sounds from which the pulse sequence sound has been eliminated are transferred to the operator through the sound output unit 114 whose output level has increased. Since the output level of the sound output unit 114 is automatically adjusted, the operator can concentrate his or her attention on scanning without having to manually adjust the sound output unit 114.

For bidirectional communication between a patient and an operator, a sound output unit through which the operator's voice is output, other than the sound input unit 157, may be further provided inside the bore 150, and a sound input unit for allowing the operator to input his or her voice in order to transfer a message to the patient lying inside the bore 150 may be further provided in the workstation 110. The sound output unit 114 can be, for example a speaker, and the sound input unit 157 can be, for example a microphone.

Also, it within the spirit and scope of the invention to control the sound output unit 114 to adjust the output level of the sound output unit 114 only when sounds generated by different causes from pulse sequences are a patient's voice.

In this case, if a sound acquired by the sound input unit 157 is not identical to a pulse sequence sound, a part of the sound corresponding to the pulse sequence sound is eliminated from the acquired sound to extract a sound generated by causes other than from the pulse sequence.

The extracted sound is compared to a patient's voice stored in advance, and if the pattern of the extracted sound is identical to the pattern of the patient's voice, the extracted sound is determined to be the patient's voice, so that the output level of the sound output unit 114 increases to the predetermined level. In order to register the voice of a patient to be scanned, an identification procedure including a process of registering a patient's voice may be performed before scanning.

Figure 10:
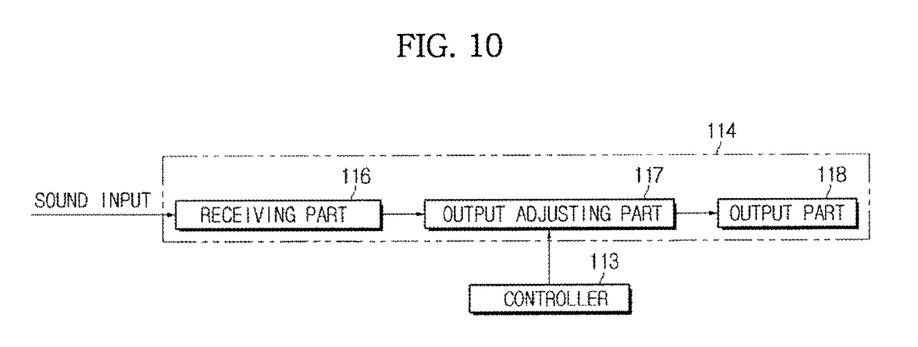
FIG. 10 is a block diagram showing the configuration of the sound output unit in detail.

FIG. 10 is a block diagram showing the configuration of the sound output unit 114 in detail.

The sound output unit 114 includes various hardware comprising a receiving part 116 for receiving a sound acquired by the sound input unit 157 (see FIG. 1), an output part 118 for outputting the sound received by the receiving part 116, and an output adjusting part 117 for comparing the sound received by the receiving part 116 to a pulse sequence sound stored in advance to adjust the output level of the output part 118.

As described above with reference to FIG. 6, the output level of the sound output unit 114 may be adjusted under the control of the workstation controller 113, or the sound output unit 114 itself may receive a sound acquired by the sound input unit 157 and adjust the output level of the sound output unit 114, like the workstation controller 113.

Figure 11:
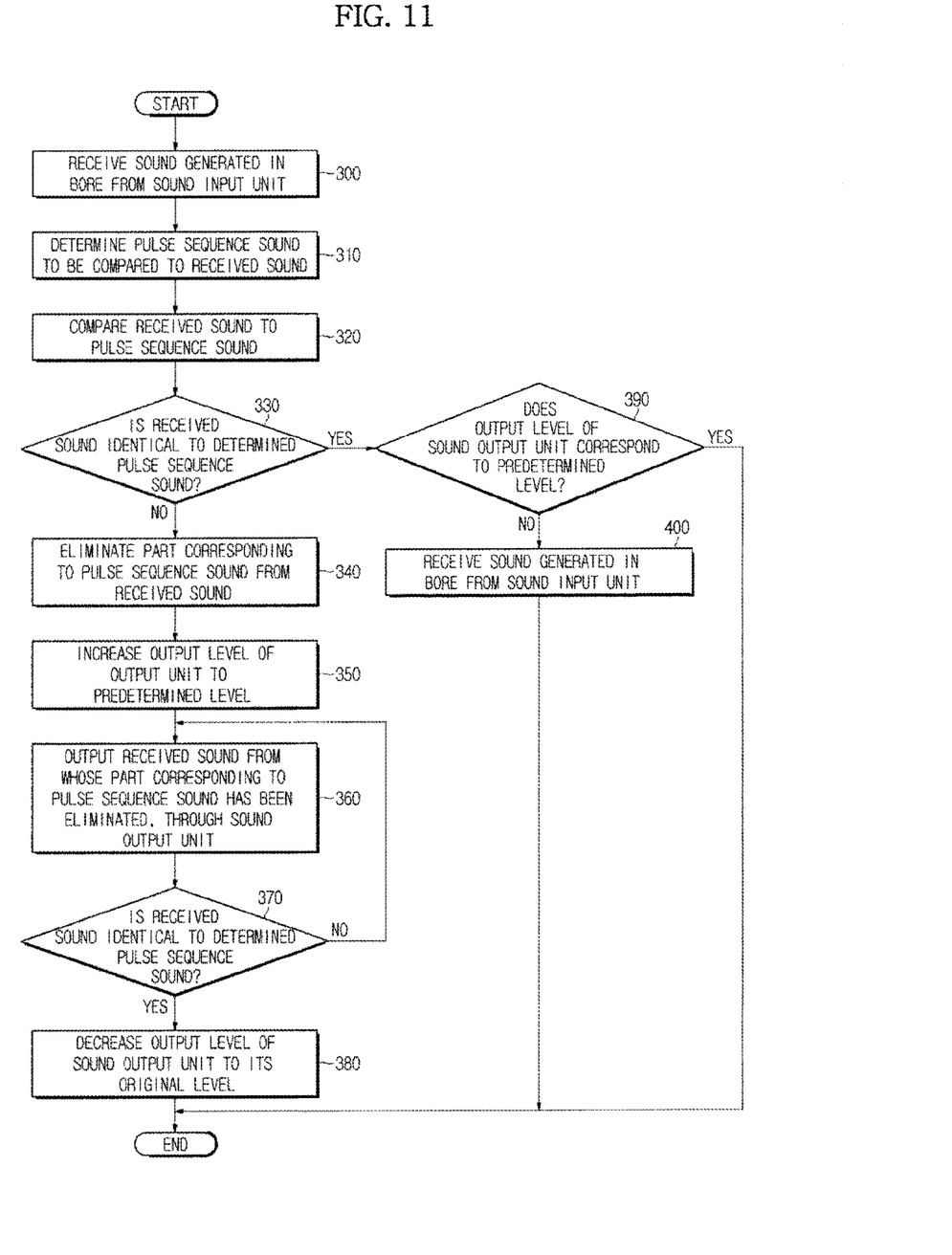
FIG. 11 is a flowchart showing exemplary operation of a control method of a MRI apparatus, in accordance with an exemplary embodiment of the present invention.

FIG. 11 is a flowchart showing a control method of a MRI apparatus, in accordance with one embodiment of the present invention.

Referring now to FIGS. 1 and 11, at (300) the sound input unit 157 acquires a sound generated in the bore 150 and transmits the sound to the workstation 110, and the controller 113 of the workstation 110 receives the sound.

The sound acquired by the sound input unit 157 may be a sound generated by a pulse sequence being used to scan a subject, or a mixed sound in which another sound, such as a patient's voice, etc., is mixed with the sound generated by the corresponding pulse sequence.

After receiving the sound generated in the bore 150 from the sound input unit 157, then at (310) the controller 113 searches for a pulse sequence sound that is to be compared to the received sound, in the sequence sound database 115, to determine a pulse sequence sound.

In other words, the controller 113 searches for sound information about a pulse sequence being currently used to scan a subject, in the sequence sound database 115, and determine a sound that is to be compared to the sound received from the sound input unit 157.

As shown in FIG. 7, the sequence sound database 115 stores sounds that are generated by various kinds of pulse sequences registered in a MRI apparatus to be used to scan a subject.

Since sounds that are generated by the same pulse sequence make the same pattern of sound, the database 115 may be established by storing sounds of individual pulse sequences.

After the pulse sequence sound is decided, at (320) the controller 113 compares the sound received from the sound input unit 157 to the pulse sequence sound.

Then at (330) the controller determines whether the received sound is identical to the pulse sequence sound.

At (330) when the received sound is not identical to the pulse sequence sound, then at (340) a part corresponding to the pulse sequence sound is eliminated from the received sound, and at (350) the output level of the sound output unit 114 increases to a predetermined level, and at (360) the resultant sound whose part corresponding to the pulse sequence sound has been eliminated is output through the sound output unit 114.

FIG. 8 shows an area at which the pattern of a sound acquired by the sound input unit 157 is not identical to the pattern of a pulse sequence sound.

If another sound, such as a patient's voice, etc., is mixed with a pulse sequence sound, a sound acquired by the sound input unit 157 has a pattern different (e.g. non-identical) from the pulse sequence sound.

When the controller 113 determines that the pattern of the received sound is not identical to the pattern of the pulse sequence sound, the controller 113 determines that another sound than the pulse sequence sound has been generated in the bore 150, and increases the output level of the sound output unit 114 located in the workstation 110 to a predetermined level in order to inform an operator of the generation of the other sound.

Generally, the output level of the sound output unit 114 is set to a minimum level close to zero. Since noise that is generated by a pulse sequence is very loud, an operator will not be able to concentrate his or her attention on scanning a subject if the noise is directly output to an operating room through the sound output unit 114, so that the operator may fail to properly scan the subject.

However, since pattern mismatch between the two sounds means that another sound than the sound caused by the pulse sequence has been generated in the bore 150, which may mean high probability that the patient experiences an unexpected situation, it is necessary to transfer the sound acquired by the sound input unit 157 through the sound output unit 114 so that the operator can recognize the situation. Accordingly, the output level of the sound output unit 114 which has output sounds at a low output level increases to the predetermined level. The predetermined level may be set to an appropriate level at which the operator can recognize a sound.

FIG. 9 is a view for explaining operation of eliminating a part corresponding to a pulse sequence sound from a sound acquired by the sound input unit 157 to filter sounds generated by different causes, not by the pulse sequence.

Since a sound that will be transferred to the operator through the sound output unit 114 does not need to include the pulse sequence sound, the pulse sequence sound is eliminated from the sound acquired by the sound input unit 157 such that only sounds generated by other causes, not by the pulse sequence are output through the sound output unit 114.

In other words, sounds from which the pulse sequence sound has been eliminated are transferred to the operator through the sound output unit 114 whose output level has increased. Since the output level of the sound output unit 114 is automatically adjusted, the operator can concentrate his or her attention on scanning without having to manually adjusting the sound output unit 114.

After (360) where the output level of the sound output unit 114 increases to the predetermined level, at (370) the controller 113 again determines whether the sound received from the sound input unit 157 is identical to the pulse sequence sound, and if the received sound is identical to the pulse sequence sound, at (380) the controller 113 decreases the output level of the sound output unit 114 to its original level to which the sound output unit 114 has been set before the output level of the sound output unit 114 increases.

The fact that the sound received from the sound input unit 157 is identical to the pulse sequence sound means that only the pulse sequence sound exists in the bore 150, and accordingly, the controller 113 returns the output level of the sound output unit 114 to its original level.

As the result of operation 320 of comparing the sound received from the sound input unit 157 to the pulse sequence sound, if it is determined at (330) that the received sound is identical to the pulse sequence sound, at (390) it is determined whether the output level of the sound output unit 114 corresponds to a predetermined level. If at (390) the output level of the sound output unit 114 does not correspond to the predetermined level, at (400) the controller 113 decreases the output level of the sound output unit 114 to the predetermined level. As described above, generally, the output level of the sound output unit 114 is set to a minimum level close to zero. Since noise that is generated by a pulse sequence is very loud, an operator will not be able to concentrate his or her attention on scanning a subject if the noise is directly output to an operating room through the sound output unit 114, so that the operator may fail to properly scan the subject. However, since there may be some other cases, operation 390 is performed. In other words, the predetermined level is a minimum level close to zero.

Also, it is within the spirit and scope of the invention to control the sound output unit 114 to adjust the output level of the sound output unit 114 only when sounds generated by different causes from pulse sequences are a patient's voice.

In such a case as described in the above paragraph, if a sound acquired from the sound input unit 157 is not identical to a pulse sequence sound, a part corresponding to the pulse sequence sound is eliminated from the acquired sound to extract a sound generated by different causes from the pulse sequence.

The extracted sound is compared to a patient's voice stored in advance, and if the pattern of the extracted sound is identical to the pattern of the patient's voice, the extracted sound is determined to be the patient's voice, so that the output level of the sound output unit 114 increases to a predetermined level. In other words, operation of determining whether an extracted sound is identical to a patient's voice stored in advance may be added between operation 340 and operation 350.

In order to register the voice of a patient to be scanned, an identification procedure including a process of registering a patient's voice may be performed before scanning.

It is also within the spirit and scope of the invention to have various voice samples to compare the extracted sound to identify the sound as a voice. Also as voice frequencies are considered in telephony to be 300-3000 HZ. The voice of a typical adult male will have a fundamental frequency from 85 to 180 Hz, and that of a typical adult female from 165 to 255 Hz, so there are numerous ways within the spirit and scope of the invention to determine whether the extracted sound is a patient's voice.

The above-described embodiments according to the present invention can be implemented in hardware, firmware or via the execution of software or computer code that configures hardware for operation, and is stored on a non-transitory machine readable medium such as a CD ROM, DVD, RAM, a floppy disk, a hard disk, or a magneto-optical disk, such as a floptical disk or computer code downloaded over a network originally stored on a remote recording medium or a non-transitory machine readable medium and stored on a local non-transitory recording medium, so that the methods described herein can be loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor" or "microprocessor" comprises hardware in the claimed invention. Under the broadest reasonable interpretation, the appended claims constitute statutory subject matter in compliance with 35 U.S.C. §101. The terms "unit" or "module" as used herein is to be understood under the broadest reasonable interpretation as constituting statutory subject matter under 35 U.S.C. §101 that includes hardware and does not constitute software per se. When a unit or module includes machine executable code it is to be understood that a non-transitory machine readable medium contains the machine executable code that is loaded into hardware such as a processor or controller for execution and configures the processor or controller for operation.

Although a few exemplary embodiments of the present invention have been shown and described, those of ordinary skill in the art understand and appreciate that various changes may be made in the examples shown and described herein without departing from the principles and spirit of the invention, the scope of which is defined in the claims and their equivalents.

What is claimed is:

1. A magnetic resonance imaging (MRI) apparatus, comprising:
   a sound input unit;
   a sound output unit configured to output a sound acquired by the sound input unit; and
   a controller configured to compare the acquired sound to a sound generated by a pulse sequence, and to increase an output level of the sound output unit if the acquired sound is not identical to the sound generated by the pulse sequence and to decrease the output level of the sound output unit if the acquired sound is identical to the sound generated by pulse sequence.

2. The MRI apparatus according to claim 1, further comprising a sequence sound database configured to store patterns of sounds that are respectively generated for a plurality of pulse sequences registered in the MRI apparatus when a subject is scanned according to at least one of the pulse sequences.

3. The MRI apparatus according to claim 1, wherein the controller checks a pulse sequence being used to scan a subject, receives a sound generated in a bore from the sound input unit, compares the received sound to a sound generated by the checked pulse sequence, and increases the output level of the sound output unit to a predetermined level when a pattern of the received sound is not identical to a pattern of the checked pulse sequence generated sound.

4. The MRI apparatus according to claim 1, wherein when a pattern of the acquired sound is not identical to a pattern of the pulse sequence generated sound, the controller eliminates a part corresponding to the pulse sequence generated sound from the acquired sound, increases the output level of the sound output unit to a predetermined level, and outputs the sound from which the pulse sequence generated sound has been eliminated, through the sound output unit whose output level has increased to the predetermined level.

5. The MRI apparatus according to claim 1, wherein when a pattern of the acquired sound is not identical to a pattern of the pulse sequence generated sound, the controller eliminates a part of the acquired sound corresponding to the pulse sequence generated sound from the acquired sound, and determines whether the sound from which the pulse sequence generated sound has been eliminated is identical to a subject's voice stored in advance, increases the output level of the sound output unit to a predetermined level if the sound from which the pulse sequence sound has been eliminated is identical to the subject's voice, and outputs the sound from which the pulse sequence generated sound has been eliminated, through the sound output unit whose output level has increased to the predetermined level.

6. The MRI apparatus according to claim 1, wherein when the controller determines that a pattern of the acquired sound is identical to a pattern of the pulse sequence generated sound after increasing the output level of the sound output unit, the controller decreases the output level of the sound output unit to an original level to which the sound output unit has been set before the output level of the sound output unit increases.

7. The MRI apparatus according to claim 1, wherein the sound input unit comprises a microphone.

8. The MRI apparatus according to claim 1, wherein the sound output unit comprises a speaker.

9. A sound output apparatus comprises: a receiving unit in a magnetic resonance imaging (MRI) apparatus configured to receive a sound; an output unit configured to output the sound received by the receiving unit; and an output adjusting unit configured to compare the received sound to a sound of a pulse sequence stored in advance, and to increase the output level of the output unit if the received sound is not identical to the sound of the pulse sequence and to decrease the output level of the sound output unit if the acquired sound is identical to the sound generated by the pulse sequence.

10. A control method of a magnetic resonance imaging (MRI) apparatus, comprising:
    comparing by a controller a sound acquired by a sound input unit to a sound generated by a pulse sequence; and
    increasing the output level of a sound output unit to a predetermined level when the acquired sound is not identical to the sound generated by the pulse sequence; and
    decreasing the output level of the sound output unit if the acquired sound is identical to the sound generated by pulse sequence.

11. The control method according to claim 10, wherein the comparing of the acquired sound to the sound generated by the pulse sequence stored in advance comprises:
    receiving a sound generated in a bore from the sound input unit;
    determining a pulse sequence generated sound that is to be compared to the received sound; and
    comparing the received sound to the determined pulse sequence sound.

12. The control method according to claim 11, wherein the determining of the pulse sequence generated sound that is to be compared to the received sound comprises:
    checking a pulse sequence being used to scan a subject; and
    determining a sound of the checked pulse sequence with reference to sequence sound database in which patterns of sounds that are respectively generated for a plurality of pulse sequences are stored.

13. The control method according to claim 10, wherein the increasing of the output level of the sound output unit to the predetermined level comprises:
    determining whether the acquired sound is identical to the sound of the pulse sequence;
    eliminating a part of the acquired sound corresponding to the sound generated by the pulse sequence from the acquired sound when a pattern of the acquired sound is not identical to a pattern of the generated pulse sequence sound; and
    increasing the output level of the sound output unit to a predetermined level in order to output the sound from which the sound of the generated pulse sequence has been eliminated.

14. The control method according to claim 10, wherein the increasing of the output level of the sound output unit to the predetermined level comprises:
    determining whether the acquired sound is identical to the sound generated by the pulse sequence;
    eliminating a part of the acquired sound corresponding to the generated pulse sequence sound from the acquired sound when the pattern of the acquired sound is not identical to a pattern of the generated pulse sequence sound.

15. The control method according to claim 10, further comprising determining whether the acquired sound is identical to the generated pulse sequence sound after increasing the output level of the sound output unit to the predetermined level, and decreasing, when the acquired sound is identical to the generated pulse sequence sound, the output level of the sound output unit to an original level to which the sound output unit has been set before the output level of the sound output unit increases.

16. The control method according to claim 10, wherein the sound input unit includes a microphone.

17. The control method according to claim 10, wherein the sound output unit comprises a speaker, a workstation includes the sound input unit through which a sound to be transferred to a bore is input, and the sound input unit includes a microphone.

* * * * *